United States Patent [19]

Steinberg et al.

[11] Patent Number: 4,534,874
[45] Date of Patent: Aug. 13, 1985

[54] ANTI-OXIDATIVE, ANTI-THERMAL, AND ANTI-ACTINIC DEGRADATION AMIDES OF HYDROXYPHENYLALKYLTHIO ALKANOIC ACIDS, COMPOSITIONS, AND METHOD OF USE THEREFOR

[75] Inventors: David H. Steinberg, New York; Raymond Seltzer, New City; John J. Luzzi, Carmel; Frank P. Cortolano, Valhalla, all of N.Y.

[73] Assignee: Ciba-Geigy Corporation, Ardsley, N.Y.

[21] Appl. No.: 554,040

[22] Filed: Nov. 21, 1983

[51] Int. Cl.$^3$ ............... C07D 251/04; C07D 233/02; C07D 295/04; C07D 243/00
[52] U.S. Cl. ............... 252/51.5 A; 260/239 BC; 524/98; 524/100; 524/106; 524/189; 524/241; 544/215; 544/224; 544/335; 544/399; 548/320; 548/341; 564/139; 564/142
[58] Field of Search ............... 260/192, 193, 239 BC, 260/439; 252/51.5 A; 524/98, 100, 106, 189, 241; 544/215, 224, 335, 399; 548/320, 341; 564/139, 142

[56] References Cited

U.S. PATENT DOCUMENTS 3,780,103  12/1973  Knoll ............... 260/562

OTHER PUBLICATIONS

Medvedev, et al., C.A., vol. 86 (1977), 5066m, p. 437.
Peterli, Jean Jacques et al., C.A., vol. 79 (1973), 6089p, p. 36.

*Primary Examiner*—Henry R. Jiles
*Assistant Examiner*—J. G. Mullins
*Attorney, Agent, or Firm*—Harry Falber

[57] ABSTRACT

The title compounds correspond to the formula

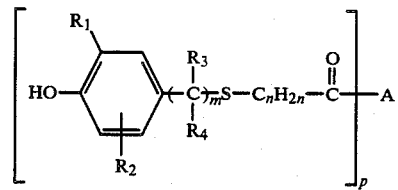

wherein A is a monovalent, bivalent, trivalent or tetravalent radical of a mono-, di-, tri- or tetraamine. These compounds are useful as stabilizers for organic polymers and lubricating oils to counteract the degradative effects of heat, light and air.

20 Claims, No Drawings

ANTI-OXIDATIVE, ANTI-THERMAL, AND ANTI-ACTINIC DEGRADATION AMIDES OF HYDROXYPHENYLALKYLTHIO ALKANOIC ACIDS, COMPOSITIONS, AND METHOD OF USE THEREFOR

Organic polymeric materials such as plastics and resins, and lubricating and mineral oils are subject to thermal, oxidative and photo-degradation. A great variety of stabilizers are known in the art for stabilizing a diversity of substrates. Their effectiveness varies depending upon the causes of degradation and the substrate stabilized. In general, it is difficult to predict which stabilizer will be most effective and most economical for any one area of application. For example stabilizer effectiveness in reducing volatility may depend upon bond scission in the substrate molecule. Limiting embrittlement and retaining elasticity in a polymer or rubber may require prevention of crosslinking and/or chain scission. Prevention of discoloration may require inhibiting reactions which yield new chromophores or color bodies in the substrate or stabilizer. Problems of process stability and incompatibility must also be considered.

It has now been determined that the hydroxyphenylalkylthio alkanoyl amide derivatives of this invention possess an unusual combination of desirable properties which make them particularly effective and useful as stabilizers. The compounds are particularly effective in protecting polyolefins, high impact polystyrene, rubbers such as polybutadiene and styrene-butadiene rubber, and other elastomers wherein retention of elasticity and inhibition of cross-linking, crazing, discoloration, odor formation and exudation are basic requirements.

A number of hindered phenol amide derivatives containing a sulfur linkage have been previously disclosed as stabilizers for organic material normally subject to oxidative deterioration, e.g., hydroxybenzyl amides of thioalkanoic acids in U.S. Pat. No. 3,780,103; hydrazides of hydroxyphenylthio alkanoic acids in Chemical Abstracts 86, 5066m (1977) and arylsulfonamides of hydroxyphenylthio alkanoic acids in Chemical Abstracts 79, 6089p (1973).

It is the primary object of this invention to provide a class of amides of hydroxyphenylalkylthio alkanoic acids which exhibits a broad range of improved stabilization performance characteristics.

Various other objects and advantages of this invention will become evident from the following description thereof.

The compounds of this invention correspond to the formula I

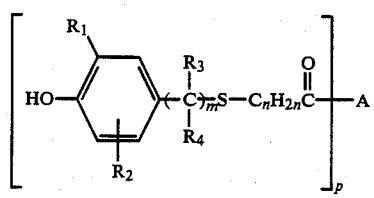

wherein:
p and n are independently 1 to 4;
m is 1 or 2;
$R_1$ and $R_2$ are independently alkyl of 1 to 12 carbon atoms, cycloalkyl of 5 to 6 carbon atoms, phenyl, phenyl substituted by alkyl of 1 to 12 carbon atoms, aralkyl of 7 to 9 carbon atoms or said aralkyl substituted by alkyl of 1 to 12 carbon atoms, and $R_2$ additionally can be hydrogen;
$R_3$ and $R_4$ are independently hydrogen, alkyl of 1 to 12 carbon atoms or phenyl;
A when p=1 is a group -NHR$_5$, wherein R$_5$ is hydrogen, amino, alkyl of 1 to 18 carbon atoms or a group of the formula

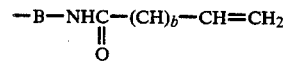

wherein:
b is 0 to 2 and B is a direct bond or alkylene of 1 to 10 carbon atoms;
A when p=2 is a bivalent radical of a 5–7 membered heterocyclic compound containing two nitrogen atoms in the ring, with the free valencies on the two nitrogen atoms, or is a group —HN—B—NH—, wherein B has the meaning given above;
A when p=3 is a group of the formula

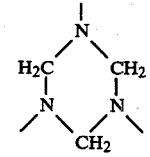

or of the formula

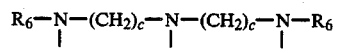

wherein:
c is 2 to 6 and $R_6$ is hydrogen or alkyl of 1 to 4 carbon atoms; and
A when p=4 is a group of formula

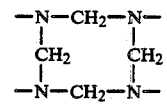

or of the formula

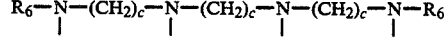

wherein c and $R_6$ have the meanings given above.

Preferred compounds within the above structure are those wherein $R_2$ is in the ortho position to the hydroxy group, $R_1$ is tert-butyl and $R_2$ is methyl or tert-butyl. $R_3$ and $R_4$ are preferably hydrogen.

$C_1$–$C_{12}$ alkyl radicals are straight-chain or branched alkyl such as, e.g., methyl, ethyl, n-propyl, isopropyl, n-butyl, sec-butyl, tert-butyl, n-pentyl, tert-pentyl, n-hexyl, 2-ethylhexyl, n-octyl, 1,1,3,3-tetramethylbutyl, decyl or dodecyl. Preferred are $C_1$–$C_8$ alkyl radicals. $R_5$ as $C_1$–$C_{18}$ alkyl is the same as defined above and is additionally e.g. tridecyl, tetradecyl, hexadecyl and octadecyl. $R_3$ is preferably $C_4$–$C_{12}$ alkyl. $R_6$ as $C_1$–$C_4$ alkyl is for example, methyl, propyl, n-butyl and preferably ethyl.

$C_5$–$C_6$ cycloalkyl is cyclopentyl or preferably cyclohexyl.

When $R_1$ and $R_2$ are aralkyl, they represent for instance benzyl, α-methylbenzyl or α,α-dimethylbenzyl.

Phenyl substituted by alkyl is e.g. tolyl, mesityl or xylyl.

B as $C_1$–$C_{10}$ alkylene is, for example, methylene, ethylene, propylene, trimethylene, 2,2-dimethylpropane-1,3- diyl, tetramethylene, pentamethylene, hexamethylene, octamethylene or decamethylene, and is preferably straight-chain $C_1$–$C_6$ alkylene.

If p is 2 and A is the radical of a heterocyclic compound containing two nitrogen atoms, preferred examples are

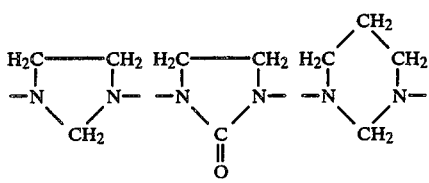

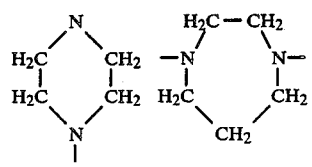

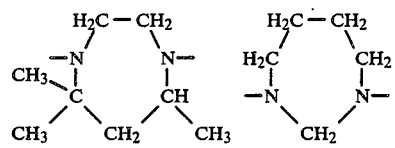

Preferred compounds of formula I are those wherein p is 2, m is 1 and n preferably 1 or especially 2. $R_5$ as a group

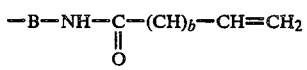

is preferably

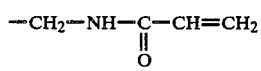

A when p=1 is preferably a group —$NHR_5$, wherein $R_5$ is alkyl of 4 to 12 carbon atoms. A when p=2 is preferably a group HN—B—NH—, wherein B is straight-chain alkylene of 1 to 6 carbon atoms. A when p=3 2 is preferably a group of the formula

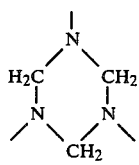

The compounds of this invention can be prepared by reacting, according to known methods, about p moles of a hydroxyphenylalkylmercaptan of formula II

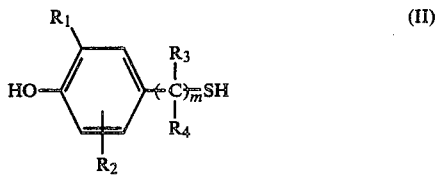

with about 1 mole of an acrylamide of Formula III

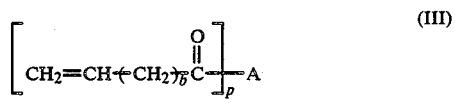

wherein A, $R_1$, $R_2$, $R_3$, $R_4$, b, m and p have the meanings given above, in the presence of a proton acceptor and preferably of a solvent.

Typical proton acceptors include lithium salts, tertiary amines, alkali metals, alkali metal and alkaline earth metal hydroxides, carbonates, and the like. The solvent is preferably a polar solvent such as (a) tetrahydrofuran, dimethylformamide, alcohols or (b) aromatic solvents and the like when acid halides are employed. The reaction temperature generally ranges from 25° to 50° C. Another method for preparing compounds of this invention involves reacting according to known methods about p moles of a thioalkanoyhalide or thioalkanoate of the formula IV

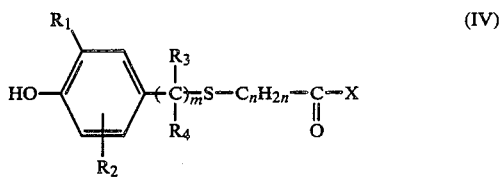

with about 1 mole of an amine of the formula V

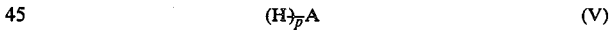

wherein A, $R_1$, $R_2$, $R_3$, $R_4$, m, n and p have the meanings given above and X is chlorine or bromine or a group—$OR_7$, wherein $R_7$ is methyl or ethyl, in the presence of the above noted solvents of group (b) and a proton acceptor.

The starting materials utilized to prepare the compounds of the present invention are items of commerce or can be prepared by known methods.

Compounds of this invention are particularly effective in stabilizing organic materials such as plastics, polymers and resins in addition to mineral and synthetic fluids such as lubricating oils, circulating oils, etc.

Substrates in which the compounds of this invention are particularly useful are polyolefins such as polyethylene and polypropylene; polystyrene, including especially impact polystyrene; ABS resin; elastomers such as e.g. butadiene rubber, EPM, EPDM, SBR and nitrile rubber.

In general polymers which can be stabilized include
1. Polymers of monoolefins and diolefins, for example polyethylene (which optionally can be crosslinked), polypropylene, polyisobutylene, polybutene-1, polymethylpentene-1, polyisoprene or polybutadiene, as well as polymers of cycloolefins, for instance of cyclopentene, cyclopentadiene or norbornene.

2. Mixtures of the polymers mentioned under (1), for example mixtures of polypropylene with polyisobutylene.

3. Copolymers of monoolefins and diolefins with each other or with other vinyl monomers, such as, for example, ethylene/propylene, propylene/butene-1, propylene/isobutylene, ethylene/butene-1, propylene/butadiene, isobutylene/isoprene, ethylene/alkyl acrylates, ethylene/alkyl methacrylates, ethylene/vinyl acetate or ethylene/acrylic acid copolymers and their salts (ionomers) and terpolymers of ethylene with propylene and a diene, such as hexadiene, dicyclopentadiene or ethylidene-norbornene.

4. Polystyrene, poly-(p-methylstyrene).

5. Copolymers of styrene or methylstyrene with dienes or acrylic derivatives, such as, for example, styrene/butadiene, styrene/acrylonitrile, styrene/ethyl methacrylate, styrene/butadiene/ethyl acrylate, styrene/acrylonitrile/methyl acrylate; mixtures of high impact strength from styrene copolymers and another polymer, such as, for example, from a polyacrylate, a diene polymer or an ethylene/propylene/diene terpolymer; and block polymers of styrene, such as, for example, styrene/butadiene/styrene, styrene/isoprene/styrene, styrene/ethylene/butylene/styrene or styrene/ethylene/propylene/styrene.

6. Graft copolymers of styrene, such as, for example, styrene on polybutadiene, styrene and acrylonitrile on polybutadiene, styrene and alkyl acrylates or methacrylates on polybutadiene, styrene and acrylonitrile on ethylene/propylene/diene terpolymers, styrene and acrylonitrile on polyacrylates or polymethacrylates, styrene and acrylonitrile on acrylate/butadiene copolymers, as well as mixtures thereof with the copolymers listed under (5), for instance the copolymer mixtures known as ABS-, MBS-, ASA-or AES-polymers.

7. Halogen-containing polymers, such as polychloroprene, chlorinated rubbers, chlorinated or sulfochlorinated polyethylene, epichlorohydrine homo- and copolymers, polymers from halogen-containing vinyl compounds, as for example, polyvinylchloride, polyvinylidene chloride, polyvinyl fluoride, polyvinylidene fluoride, as well as copolymers thereof, as for example, vinyl chloride/vinylidene chloride, vinyl chloride/vinyl acetate or vinylidene chloride/vinyl acetate copolymers.

8. Polymers which are derived from $\alpha,\beta$-unsaturated acids and derivatives thereof, such as polyacrylates and polymethacrylates, polyacrylamide and polyacrylonitrile.

9. Copolymers from the monomers mentioned under (8) with each other or with other unsaturated monomers, such as, for instance, acrylonitrile/butadiene, acrylonitrile/alkyl acrylate, acrylonitrile/alkoxyalkyl acrylate or acrylonitrile/vinyl halogen copolymers or acrylonitrile/alkyl methacrylate/butadiene terpolymers.

10. Polymers which are derived from unsaturated alcohols and amines, or acyl derivatives thereof or acetals thereof, such as polyvinyl alcohol, polyvinyl acetate, polyvinyl stearate, polyvinyl benzoate, polyvinyl maleate, polyvinylbutyral, polyallyl phthalate or polyallyl-melamine.

11. Homopolymers and copolymers of cyclic ethers, such as polyalkylene glycols, polyethylene oxide, polypropylene oxide or copolymers thereof with bis-glycidyl ethers.

12. Polyacetals, such as polyoxymethylene and those polyoxymethylenes which contain ethylene oxide as comonomer.

13. Polyphenylene oxides and sulfides, and mixtures of polyphenylene oxides with polystyrene.

14. Polyurethanes which are derived from polyethers, polyesters or polybutadienes with terminal hydroxyl groups on the one side and aliphatic or aromatic polyisocyanates on the other side, as well as precursors thereof (polyisocyanates, polyols or prepolymer).

15. Polyamides and copolyamides which are derived from diamines and dicarboxylic acids and/or from aminocarboxylic acids or the corresponding lactams, such as polyamide 4, polyamide 6, polyamide 6/6, polyamide 6/10, polyamide 11, polyamide 12, poly-2,4,4-trimethylhexamethylene terephthalamide or poly-m-phenylene isophthalamide, as well as copolymers thereof with polyethers, such as for instance with polyethylene glycol, polypropylene glycol or polytetramethylene glycols.

16. Polyureas, polyimides and polyamide-imides.

17. Polyesters which are derived from dicarboxylic acids and diols and/or from hydroxycarboxylic acids or the corresponding lactones, such as polyethylene terephthalate, polybutylene terephthalate, poly-1,4-dimethylol-cyclohexane terephthalate, poly-[2,2-(4-hydroxyphenyl)-propane]terephthalate and polyhydroxybenzoates as well as block-copolyether-esters derived from polyethers having hydroxyl end groups.

18. Polycarbonates.

19. Polysulfones, polyethersulfones and polyetherketones.

20. Crosslinked polymers which are derived from aldehydes on the one hand and phenols, ureas and melamines on the other hand, such as phenol/formaldehyde resins, urea/formaldehyde resins and melamine/formaldehyde resins.

21. Drying and non-drying alkyd resins.

22. Unsaturated polyester resins which are derived from copolyesters of saturated and unsaturated dicarboxylic acids with polyhydric alcohols and vinyl compounds as crosslinking agents, and also halogen-containing modifications thereof of low inflammability.

23. Thermosetting acrylic resins, derived from substituted acrylic esters, such as epoxy-acrylates, urethane-acrylates or polyester acrylates.

24. Alkyd resins, polyester resins or acrylate resins in admixture with melamine resins, urea resins, polyisocyanates or epoxide resins as crosslinking agents.

25. Crosslinked epoxide resins which are derived from polyepoxides, for example from bis-glycidyl ethers or from cycloaliphatic diepoxides.

26. Natural polymers, such as cellulose, rubber, gelatine and derivatives thereof which are chemically modified in a polymerhomologous manner, such as cellulose acetates, cellulose propionates and cellulose butyrates, or the cellulose ethers, such as methylcellulose.

27. Mixtures of polymers as mentioned above, for example PP/EPDM, Polyamide 6/EPDM or ABS, PVC/EVA, PVC/ABS, PVC/MBC, PC/ABS, PBTP/ABS.

28. Naturally occuring and synthetic organic materials which are pure monomeric compounds or mixtures of such compounds, for example mineral oils, animal and vegetable fats, oil and waxes, or oils, fats and waxes based on synthetic esters (e.g. phthalates, adipates, phosphates or trimellitates) and also mixtures of synthetic esters with mineral oils in any weight ratios, which materials may be used as plasticizer for polymers or as textile spinning oils, as well as aqueous emulsions of such materials.

29. Aqueous emulsions of natural or synthetic rubber, e.g. natural latex or latices of carboxylated styrene/-butadiene copolymers.

In general, the stabilizers of this invention are employed in from about 0.01 to about 5% by weight of the stabilized composition, although this will vary with the particular substrate and application. An advantageous range is from about 0.05 to about 2%, and especially 0.1 to about 1%.

The stabilizers of the instant invention may readily be incorporated into the organic polymers by conventional techniques, at any convenient stage prior to the manufacture of shaped articles therefrom. For example, the stabilizer may be mixed with the polymer in dry powder form, or a suspension or emulsion of the stabilizer may be mixed with a solution, suspension, or emulsion of the polymer. The stabilized polymer compositions of the invention may optionally also contain various conventional additives, such as the following.

1. Antioxidants 1.1. Alkylated monophenols, for example,
2,6-di-tert.butyl-4-methylphenol
2-tert.butyl-4,6-dimethylphenol
2,6-di-tert.butyl-4-ethylphenol
2,6-di-tert.butyl-4-n-butylphenol
2,6-di-tert.butyl-4-i-butylphenol
2,6-di-cyclopentyl-4-methylphenol
2-($\alpha$-methylcyclohexyl)-4,6-dimethylphenol
2,6-di-octadecyl-4-methylphenol
2,4,6-tri-cyclohexylphenol
2,6-di-tert.butyl-4-methoxymethylphenol 1.2. Alkylated hydroquinones, for example,
2,6-di-tert.butyl-4-methoxyphenol
2,5-di-tert.butyl-hydroquinone
2,5-di-tert.amyl-hydroquinone
2,6-diphenyl-4-octadecyloxyphenol 1.3. Hydroxylated thiodiphenyl ethers, for example
2,2'-thio-bis-(6-tert.butyl-4-methylphenol)
2,2'-thio-bis-(4-octylphenol)
4,4'-thio-bis-(6-tert.butyl-3-methylphenol)
4,4'-thio-bis-(6-tert.butyl-2-methylphenol)

1.4. Alkylidene-bisphenols, for example,
2,2'-methylene-bis-(6-tert.butyl-4-methylphenol)
2,2'-methylene-bis-(6-tert.butyl-4-ethylphenol)
2,2'-methylene-bis-[4-methyl-6-($\alpha$-methylcyclohexyl)-phenol]
2,2'-methylene-bis-(4-methyl-6-cyclohexylphenol)
2,2'-methylene-bis-(6-nonyl-4-methylphenol)
2,2'-methylene-bis-[6-($\alpha$-methylbenzyl)-4-nonylphenol]
2,2'-methylene-bis-[6-($\alpha,\alpha$-dimethylbenzyl)-4-nonylphenol]
2,2'-methylene-bis-(4,6-di-tert.butylphenol)
2,2'-ethylidene-bis-(4,6-di-tert.butylphenol)
2,2'-ethylidene-bis-(6-tert.butyl-4-isobutylphenol)
4,4'-methylene-bis-(2,6-di-tert.butylphenol)
4,4'-methylene-bis-(6-tert.butyl-2-methylphenol)
1,1-bis-(5-tert.butyl-4-hydroxy-2-methylphenyl-butane
2,6-di-(3-tert.butyl-5-methyl-2-hydroxybenzyl)-4-methylphenol
1,1,3-tris-(5-tert.butyl-4-hydroxy-2-methylphenyl)-butane
1,1-bis-(5-tert.butyl-4-hydroxy-2-methylphenyl)-3-n-dodecylmercaptobutane
ethylenglycol-bis-[3,3-bis-(3'-tert.butyl-4'-hydroxyphenyl)butyrate]
di-(3-tert.butyl-4-hydroxy-5-methylphenyl)-dicyclopentadiene
di-[2-(3'-tert.butyl-2'-hydroxy-5'-methyl-benzyl)-6-tert.butyl-4-methylphenyl]-terephthalate.

1.5. Benzyl compounds, for example,
1,3,5-tri-(3,5-di-tert.butyl-4-hydroxybenzyl)-2,4,6-trimethylbenzene
bis-(3,5-di-tert.butyl-4-hydroxybenzyl)-sulfide
3,5-di-tert.butyl-4-hydroxybenzyl-mercapto-acetic acid isooctyl ester
bis-(4-tert.butyl-3-hydroxy-2,6-dimethylbenzyl)dithiolterephthalate
1,3,5-tris-(3,5-di-tert.butyl-4-hydroxybenzyl)-isocyanurate
1,3,5-tris-(4-tert.butyl-3-hydroxy-2,6-dimethylbenzyl)-isocyanurate
3,5-di-tert.butyl-4-hydroxybenzyl-phosphoric acid-dioctadecyl ester
3,5-di-tert.butyl-4-hydroxybenzyl-phosphoric acid-monoethyl ester, calcium-salt 1.6. Acylaminophenols, for example,
4-hydroxy-lauric acid anilide
4-hydroxy-stearic acid anilide
2,4-bis-octylmercapto-6-(3,5-tert.butyl-4-hydroxyanilino)-s-triazine
octyl-N-(3,5-di-tert.butyl-4-hydroxyphenyl)-carbamate 1.7. Esters of $\beta$-(3,5-di-tert.butyl-4-hyroxyphenyl)-propionic acid with monohydric or polyhydric alcohols, for example,

| | |
|---|---|
| methanol | diethyleneglycol |
| octadecanol | triethyleneglycol |
| 1,6-hexanediol | pentaerythritol |
| neopentylglycol | tris-hydroxyethyl isocyanurate |
| thiodiethyleneglycol | di-hydroxyethyl oxalic acid diamide |

1.8. Ester of $\beta$-(5-tert.butyl-4-hydroxy-3-methylphenyl)propionic acid with monohydric or polyhydric alcohols, for example,

| | |
|---|---|
| methanol | diethyleneglycol |
| octadecanol | triethyleneglycol |
| 1,6-hexanediol | pentaerythritol |
| neopentylglycol | tris-hydroxyethyl isocyanurate |
| thiodiethyleneglycol | di-hydroxyethyl oxalic diamide |

1.9. Amides of $\beta$-(3,5-di-tert.butyl-4-hydroxyphenyl)-propionic acid for example,
N,N'-bis-(3,5-di-tert.butyl-4-hydroxyphenylpropionyl)-hexamethylenediamine
N,N'-bis-(3,5-di-tert.butyl-4-hydroxyphenylpropionyl)-trimethylenediamine
N,N'-bis-(3,5-di-tert.butyl-4-hydroxyphenylpropionyl)-hydrazine 2. UV absorbers and light stabilisers 2.1. 2-(2'-Hydroxyphenyl)-benztriazoles, for example, the 5'-methyl-, 3',5'-di-tert.butyl-, 5'-tert.butyl-, 5'-(1,1,3,3-tetramethylbutyl)-, 5-chloro-3',5'-di-tert.butyl-, 5-chloro-3'-tert.butyl-5'-methyl-, 3'-sec.butyl-5'-tert.butyl-, 4'-octyloxy, 3',5'-di-tert.amyl-, 3',5'-bis-($\alpha,\alpha$-dimethylbenzyl)-derivative.

2.2. 2-Hydroxy-benzophenones, for example, the 4-hydroxy-, 4-methoxy-, 4-octyloxy, 4-decyloxy-, 4-dodecyloxy-, 4-benzyloxy, 4,2',4'-trihydroxy- and 2'-hydroxy-4,4'-dimethoxy derivative.

2.3. Ester of optionally substituted benzoic acids for example, phenyl salicylate, 4-tert.butyl-phenylsalicylate, octylphenyl salicylate, dibenzoylresorcinol, bis-(4-tert.-butylbenzoyl)-resorcinol, benzoylresorcinol, 3,5-di-tert.-butyl-4-hydroxybenzoic acid 2,4-di-tert.butylphenyl ester and 3,5-di-tert.-butyl-4-hydroxybenzoic acid hexadecyl ester.

2.4. Acrylates, for example, α-cyano-β,β-diphenylacrylic acid ethyl ester or isooctyl ester, α-carbomethoxy-cinnamic acid methyl ester, α-cyano-β-methyl-p-methoxy-cinnamic acid methyl ester or butyl ester, α-carbomethoxy-p-methoxycinnamic acid methyl ester, N-(β-carbomethoxy-β-cyanovinyl)-2-methyl-indoline.

2.5 Nickel compounds, for example, nickel complexes of 2,2'-thio-bis-[4-(1,1,3,3-tetramethylbutyl)-phenol], such as the 1:1 or 1:2 complex, optionally with additional ligands such as n-butylamine, triethanolamine or N-cyclohexyl-di-ethanolamine, nickel dibutyldithiocarbamate, nickel salts of 4-hydroxy-3,5-di-tert.butylbenzylphosphonic acid monoalkyl esters, such as of the methyl, ethyl or butyl ester, nickel complexes of ketoximes such as of 2-hydroxy-4-methyl-phenyl undecyl ketoxime, nickel complexes of 1-phenyl-4-lauroyl-5-hydroxy-pyrazol, optionally with additional ligands.

2.6. Sterically hindered amines, for example bis-(2,2,6,6-tetramethylpiperidyl)sebacate, bis-(1,2,2,6,6-pentamethylpiperidyl)-sebacate, n-butyl-3,5-di-tert.butyl-4-hydroxybenzyl malonic acid, bis-(1,2,2,6,6-pentamethylpiperidyl)ester, condensation product of 1-hydroxyethyl-2,2,6,6-tetramethyl-4-hydroxypiperidine and succinic acid, condensation product of N,N'-(2,2,6,6-tetramethylpiperidyl)-hexamethylenediamine and 4-tert.octylamino-2,6-dichloro-1,3,5-s-triazine, tris-(2,2,6,6-tetramethylpiperidyl)-nitrilotriazetate, tetrakis-(2,2,6,6-tetramethyl-4-piperidyl)-1,2,3,4-butane-tetracarbonic acid, 1,1'(1,2-ethanediyl)-bis-(3,3,5,5-tetramethylpiperazinone).

2.7. Oxalic acid diamides, for example, 4,4'-dioctyloxyoxanilide, 2,2'-di-octyloxy-5,5'-di-tert.butyl-oxanilide, 2,2'-di-dodecyloxy-5,5'-di-tert.butyl-oxanilide, 2-ethoxy-2'-ethyl-oxanilide, N,N'-bis(3-dimethylaminopropyl)oxalamide, 2-ethoxy-5-tert.butyl-2'-ethyloxanilide and its mixture with 2-ethoxy-2'-ethyl-5,4'-di-tert.butyloxanilide and mixtures of ortho- and para-methoxy-as well as of o- and p-ethoxy-disubstituted oxanilides.

3. Metal deactivators, for example, N,N'-diphenyloxalic acid diamide, N-salicylal-N'-salicyloylhydrazine, N,N'-bis-salicyloylhydrazine, N,N'-bis-(3,5-di-tert.butyl-4-hydroxyphenylpropionyl)-hydrazine, 3-salicyloylamino-1,2,4-triazole, bis-benzylidene-oxalic acid dihydrazide.

4. Phosphites and phosphonites, for example, triphenyl phosphite, diphenylalkyl phosphites, phenyldialkyl phosphites, tri-(nonylphenyl)phosphite, trilauryl phosphite, trioctadecyl phosphite, di-stearylpentaerythrityl diphosphite, tris-(2,4-di-tert.butylphenyl)-phosphite, di-isodecylpentaerythrityl diphosphite, di-(2,4-di-tert.butylphenyl)pentaerythrityl diphosphite, tristearyl-sorbityl triphosphite, tetrakis(2,4-di-tert.butylphenyl)-4,4'-diphenylylendiphosphonite.

5. Compounds which destroy peroxide, for example, esters of β-thiodipropionic acid, for example the lauryl, stearyl, myristyl or tridecyl esters, mercapto-benzimidazole or the zinc salt of 2-mercaptobenzimidazole, zinc-dibutyl-dithiocarbamate, dioctadecyldisulfide, pentaerythrityl-tetrakis(β-dodecylmercapto)-propionate.

6. Polyamide stabilizers, for example copper salts in combination with iodides and/or phosphorus compounds and salts of divalent manganese.

7. Basic co-stabilizers, for example, melamine, polyvinylpyrrolidone, dicyandiamide, triallyl cyanurate, urea derivatives, hydrazine derivatives, amines, polyamides, polyurethanes, alkali metal salts and alkaline earth metal salts of higher fatty acids for example Ca stearate, Zn stearate, Mg stearate, Na ricinoleate and K palmitate, antimony pyrocatecholate or zinc pyrocatecholate.

8. Nucleating agents, for eample, 4-tert.butyl-benzoic acid, adipic acid, diphenylacetic acid.

9. Fillers and reinforcing agents, for example, calcium carbonate, silicates, glass fibres, asbestos, talc, kaolin, mica, barium sulfate, metal oxides and hydroxides, carbon black, graphite.

10. Other additives, for example, plasticizers, lubricants, emulsifiers, pigments, optical brighteners, flameproofing agents, anti-static agents, blowing agents and thiosynergists such as dilaurylthiodipropionate or distearylthiodipropionate.

The following examples illustrate the embodiments of this invention. In these examples, all parts given are by weight unless otherwise specified.

EXAMPLE 1

N,N'-Hexamethylene-Bis[3-(3,5-di-t-butyl-4-hydroxybenzylthio)Propionamide]

A flask equipped with stirrer, thermometer, condenser and addition funnel was charged with 13.72 grams (0.04 moles) of 3-(3,5-di-t.butyl-4-hydroxybenzylthio)propionyl chloride in 70 ml. toluene. The flask was placed in an ice bath at 5° C. and under a nitrogen atmosphere whereupon 2.32 grams of 1,6-hexanediamine (0.02 moles), 4.05 grams of triethylamine and 30 ml. of toluene were added thereto over a 30 minute period. Stirring was continued for an extended period and 50 ml. toluene was then added to facilitate the stirring. The resultant precipitate was successively washed with toluene and diethyl ether, stripped of residual solvent and the residue purified by means of chromatography. The glass thus obtained was triturated with hot cyclohexane and filtered. The resulting white crystals were then recrystallized to yield the desired product, m.p. 126°-130° C.

Anal. Calcd. for $C_{42}H_{68}N_2O_4S_2$: C, 69,2; H,9.4; S, 8.8; N, 3.8. Found: C, 69.1; H, 9.3; S, 8.7; N, 3.6.

EXAMPLES 2-4

The compounds as listed in Table I were prepared according to the general method as described in Example 1.

TABLE 1

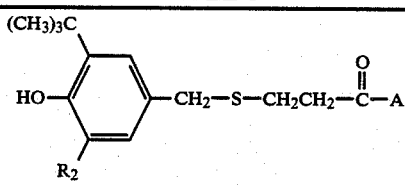

| Example | $R_2$ | A | m.p. |
|---------|-------|---|------|
| 2 | —C(CH$_3$)$_3$ | —NH—C$_{12}$H$_{25}$ | 50–55° C. |

TABLE 1-continued

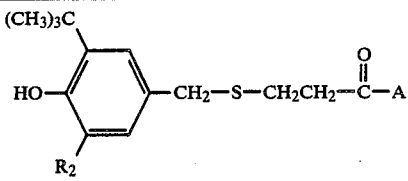

| Example | R₂ | A | m.p. |
| --- | --- | --- | --- |
| 3 | —C(CH₃)₃ | —NH—NH₂ | 104–107° C. |
| 4 | —CH₃ | —NH—NH₂ | syrup |

EXAMPLE 5

N-t.Butyl-[3-(3-t.butyl-5-methyl-4-hydroxybenzylthio)-Propionamide]

A flask fitted with stirrer, condenser, thermometer and addition funnel was placed under a nitrogen atmosphere and charged with 12.7 grams of N-t.butylacrylamide (0.10 moles), 0.2 grams of triethylamine and 100 ml. of methanol. The mixture was heated at 40° C. whereupon 22.1 grams of 3-t.butyl-5-methyl-4-hydroxybenzyl mercaptan (0.105 moles) and 50 ml. of methanol were added thereto over a one hour period. The reaction continued at 40° C. for three additional hours and then at room temperature for 18 further hours. The presence of unreacted mercaptan necessitated the addition of 0.1 grams of benzyltrimethyl ammonium fluoride as a catalyst and further reaction at 40° C. and room temperature. The methanol was then removed and purification accomplished by means of chromatography. A semi-solid product was obtained.

Anal. Calcd. for $C_{19}H_{31}NO_2S$: C, 67.6; H, 9.3; S, 9.5; N, 4.2. Found: C, 67.9; H, 8.9; S, 9.3; N, 4.3.

EXAMPLES 6–10

The compounds as listed in Table II were prepared according to the general method as described in Example 5.

TABLE II

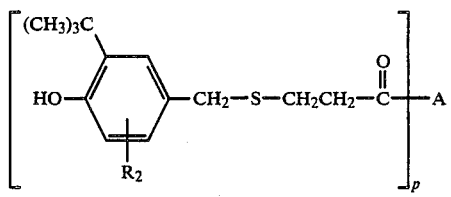

| Example | p | R₂ | A | m.p. |
| --- | --- | --- | --- | --- |
| 6 | 1 | —CH₃ | —NH₂ | syrup |
| 7 | 2 | —C(CH₃)₃ | —HN—CH₂—NH— | 182–189° C. |
| 8 | 2 | —CH₃ | —HN—CH₂—NH— | 108–111° C. |
| 9 | 3 | —C(CH₃)₃ | 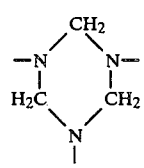 | 139–142° C. |

TABLE II-continued

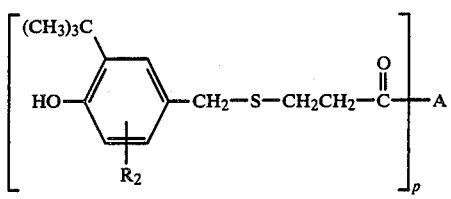

| Example | p | R₂ | A | m.p. |
| --- | --- | --- | --- | --- |
| 10 | 3 | —CH₃ | 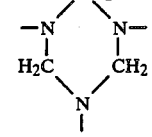 | 160–161° C. |

EXAMPLE 11

N-Dodecyl-(3,5-di-t-butyl-4-hydroxybenzylthio) Acetamide

A flask fitted with stirrer, thermometer and condenser, under nitrogen, was charged with 18.54 grams of n-dodecylamine (0.1 moles) and 9.21 grams of thioglycolic acid (0.1 moles). The resulting slurry was allowed to react at 140° C. for 10 hours. Thereafter, 26.35 grams of 2,6-di-t.butyl-4-dimethyl-aminomethyl phenol (0.1 moles) and 100 ml. isopropanol were added to the anticipated in-situ reaction product, i.e. N-dodecyl-β-mercaptoacetamide. The reaction continued at reflux (80° C.) for ten hours. The isopropanol was removed and the product isolated by flash chromatography. Off-white crystals with m.p. 43°–46° C. were recovered after removal of the solvent in vacuo.

Anal. Calcd. for $C_{29}H_{51}NO_2S$; C, 72.9; H, 10.8; S, 6.7; N, 2.9. Found: C, 73.0; H, 10.8; S, 6.7; N, 3.0.

EXAMPLE 12

This example illustrates the stabilizing effectiveness of the instant stabilizers in impact polystyrene.

In a laboratory procedure utilized herein, a solution of eight (8) weight percent polybutadiene rubber (Firestone-DIENE 55) dissolved in styrene monomer is prepared on a roller mill. The indicated amount of stabilizer is also introduced at this point. 500 ppm of zinc stearate are added to aid in removing the sample from the bottle after the polymerization. The bottle is screwed into the polymerization apparatus which is equipped with a double helical ribbon stirrer. Since most commercial IPS bulk polymerizations are thermally initiated processes, no initiator is used in the laboratory process. A nitrogen atmosphere is established and the reactor is then heated to 121° C. within ½ hour. Heating continues at 121° C. with efficient stirring until there is a 30 to 35% monomer conversion (2.5 hours). The stirring rate is controlled to yield a two to four m rubber particle size. The bottles are removed from the polymerization apparatus, blanketed with nitrogen, capped, and then placed in a fluidized bed sand bath to complete the polymerization. The bottles are heated in the bath in the following fashion: one hour at 100° C. to equilibrate the temperature, one hour to reach 140° C. and then an additional eight hours with the temperature increasing at the rate of 10° C. per hour to a maximum of 220° C. After the resin has cooled, the bottle is broken and the glass removed. The average weight of the polymer block is slightly over 600 grams. The block is then placed into a vacuum oven at 200° C. and a vacuum of 1 mm applied as the polymer is heated for 45 minutes in order to remove all volatiles. The block is removed from the oven, immediately placed in a heated (205° C.) hydraulic press and then pressed into a thick slab between two sheets of aluminum foil (three minutes heating, five minutes in a cold press). The slab is split with a hand saw and the pieces are granulated.

All batches are extruded at 205° C. and then pelletized. The pellets are compression molded at 205° C. into 125 mil (3.175 mm) tensile bars. The bars are then aged at 150° C. on glass plates placed on rotating shelves in a forced air oven. Other tensile bars are aged at 80° C. suspended from rotating shelves in a forced air oven. The specimen yellowness index is determined on the bars at various intervals according to ASTM D-1925-63T. Correspondingly, the bars are periodically measured for percent elongation in the Instron Tensile Testing Apparatus (Instron Engineering Corporation, Massachusetts) at a pull rate of 5 mm/minute according to ASTM D-638.

Oven Aged Samples at 80° C.

| Additive | Additive Conc. (% by weight) | Hours at 80° C. | | | |
|---|---|---|---|---|---|
| | | 0 | 300 | 600 | 900 |
| | | % Elongation | | | |
| none | — | 33 | 9 | 3 | 3 |
| Example 6 | 0.1 | 47 | 36 | 29 | 24 |
| Example 7 | 0.1 | 58 | 35 | 31 | 28 |
| Example 8 | 0.1 | 56 | 38 | 35 | 29 |
| Example 10 | 0.1 | 51 | 36 | 28 | 30 |
| Example 7 + DLTDP* | 0.05/0.05 | 64 | 35 | 19 | 11 |
| | | Yellowness Index | | | |
| none | — | 7 | 14 | 45 | 59 |
| Example 6 | 0.1 | −11 | −5 | 2 | 13 |
| Example 7 | 0.1 | −11 | −3 | −2 | 8 |
| Example 8 | 0.1 | −11 | −4 | 2 | 5 |
| Example 10 | 0.1 | −11 | −2 | 6 | 16 |
| Example 7 + DLTDP* | 0.05/0.05 | −3 | 4 | 15 | 39 |

Oven Aged Samples at 150° C.

| Additive | Additive Conc. (% by weight) | Hours at 150° C. | | | | |
|---|---|---|---|---|---|---|
| | | 0 | ½ | 1 | 1½ | 2 |
| | | % Elongation | | | | |
| none | — | 33 | 7 | 7 | 3 | 3 |
| Example 6 | 0.1 | 47 | 25 | 24 | 26 | — |
| Example 7 | 0.1 | 58 | 44 | 32 | 37 | 28 |
| Example 8 | 0.1 | 56 | 32 | 50 | 31 | 33 |
| Example 10 | 0.1 | 51 | 40 | 36 | 35 | — |
| Example 7 + DLTDP* | 0.05/0.05 | 64 | 56 | 36 | 45 | 45 |
| | | Yellowness Index | | | | |
| none | — | 7 | 18 | 30 | 38 | 43 |
| Example 6 | 0.1 | −11 | −9 | −8 | −8 | −7 |
| Example 7 | 0.1 | −11 | −9 | −8 | −8 | −6 |
| Example 8 | 0.1 | −11 | −9 | −7 | −7 | −4 |
| Example 10 | 0.1 | −11 | −8 | −8 | −3 | — |
| Example 7 + DLTP* | 0.05/0.05 | −3 | −1 | 0 | 2 | 2 |

*Dilaurylthiodipropionate

EXAMPLE 13

The example illustrates the stabilizing effectiveness of the instant stabilizers in ABS resin.

The following acrylonitrile-butadiene-styrene latex was prepared by adding the emulsion component to the ABS latex and blending thoroughly.

| | parts |
|---|---|
| ABS latex (40%, by wt., rubber) | 625 |
| Compound of Ex. 2 | 5 |
| Toluene | 40 |
| Alkyl aryl polyether alcohol (Triton X-100) | 4 |
| Water | 150 |

A comparable control latex was prepared without the stabilizer. In each instance, the resulting latex was added to a 15%, by weight, aqueous solution of sodium sulfate at 90° C. in order to coagulate the system. The mixture was then filtered and the solids washed five times with 90° C. water. The wet solids from the filter cake were then subjected to a differential scanning calorimetry (DSC) procedure in order to test thermal stability, the higher Tmax values being indicative of greater thermal stability. The results obtained were as follows:

| | DSC (dynamic) Tmax (°C.) |
|---|---|
| Control (no stabilizer) | 160 |
| Stabilized latex (Ex. 2) | 215 |

Examples 12 and 13 thus indicate the significantly better performance provided by the instant compounds as compared to the base resin.

Summarizing, it is seen that this invention provides a group of compounds which exhibit meaningful stabilizing activity in a variety of organic materials. Variations may be made in proportions, procedures and materials without departing from the scope of the invention as defined by the following claims.

We claim:

1. The compound of the formula I

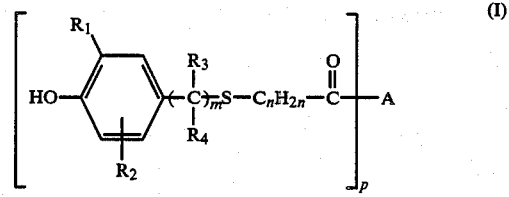

wherein
p and n are independently 1 to 4;
m is 1 or 2;
$R_1$ and $R_2$ are independently alkyl of 1 to 12 carbon atoms, cycloalkyl of 5 to 6 carbon atoms, phenyl, phenyl substituted by alkyl of 1 to 12 carbon atoms, aralkyl of 7 to 9 carbon atoms or said aralkyl substituted by alkyl of 1 to 12 carbon atoms and $R_2$ additionally can be hydrogen;
$R_3$ and $R_4$ are independently hydrogen, alkyl of 1 to 12 carbon atoms or phenyl;
A when p=1 is a group $-NHR_5$, $R_5$ is hydrogen, alkyl of 1 to 18 carbon atoms or a group of the formula

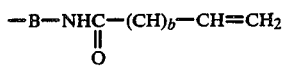

wherein
b is 0 to 2 and B is a direct bond or alkylene of 1 to 10 carbon atoms;
A when p=2 is a group of the formulae

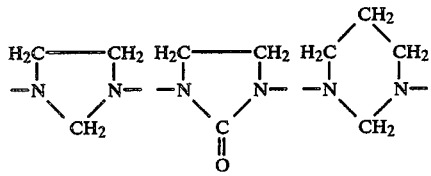

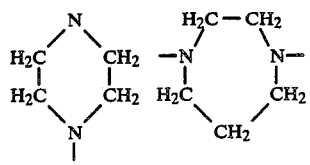

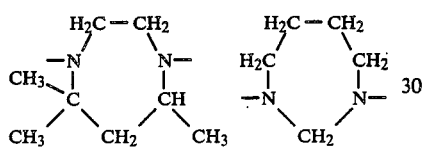

or is a group —NH—B—NH—, wherein B has the meaning given above;
A when p=3 is a group of the formula

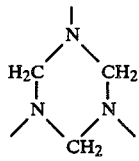

or of the formula

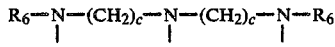

wherein
c is 2 to 6 and $R_6$ is alkyl of 1 to 4 carbon atoms; and
A when p=4 is a group of formula

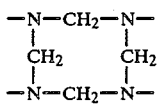

or of formula

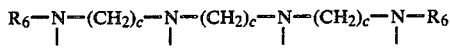

wherein c and $R_6$ have the meanings given above.

2. The compound of claim 1, wherein $R_2$ is in the ortho position to the hydroxy group.

3. The compound of claim 2, wherein $R_1$ is tert-butyl and $R_2$ is methyl or tert-butyl.

4. The compound of claim 1, wherein p is 2.

5. The compound of claim 1, wherein m is 1.

6. The compound of claim 1, wherein n is 1 or 2.

7. The compound of claim 6, wherein n is 2.

8. The compound of claim 1, wherein $R_5$ is —CH$_2$—NH—C(O)—CH=CH$_2$.

9. The compound of claim 1, wherein p is 1 and A is —NHR$_3$, wherein $R_3$ is alkyl of 4 to 12 carbon atoms.

10. The compound of claim 1, wherein p is 2 and A is —HN—B—NH— wherein B is straight-chain alkylene of 1 to 6 carbon atoms.

11. The compound of claim 1, wherein p is 3 and A is a group of the formula

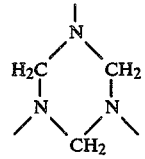

12. N,N'-Methylene-bis-[3-(3-tert-butyl-5-methyl-4-hydroxybenzylthio)propionamide] according to claim 1.

13. N,N'-Hexamethylene-bis-[3-(3,5-di-tert-butyl-4-hydroxybenzylthio)propionamide] according to claim 1.

14. N,N'-Methylene-bis-[3-(3,5-di-tert-butyl-4-hydroxybenzylthio)propionamide] according to claim 1.

15. N,N',N''-Tris-[3-(3,5-di-tert-butyl-4-hydroxybenzylthio)propionyl]hexahydrotriazine according to claim 1.

16. N-Dodecyl-[3-(3,5-di-tert-butyl-4-hydroxybenzylthio)propionamide] according to claim 1.

17. A composition of matter comprising polymers or lubricating oils subject to oxidative, thermal and actinic degradation stabilized with an effective stabilizing amount of a compound of claim 1.

18. The composition of claim 17, wherein the organic material is a synthetic polymer.

19. The composition of claim 18, wherein said polymer is selected from the group consisting of polyolefins, impact polystyrene, acrylonitrile/butadiene/styrene resin, butadiene rubber, ethylene/propylene rubbers, styrene/butadiene rubber and nitrile rubber.

20. A method for stabilizing polymers or lubricating oils against oxidative, thermal and actinic degradation which comprises incorporating into said organic material an effective stabilizing amount of a compound of claim 1.

* * * * *